United States Patent
Dubois et al.

(10) Patent No.: US 9,254,331 B2
(45) Date of Patent: Feb. 9, 2016

(54) SULFORAPHANE STABILIZATION

(75) Inventors: Jacques Dubois, Villers-la-ville (BE);
Alfred Marchal, Waterloo (BE);
Damien Lacroix, Ernage (BE); Jérôme Cabou, Saint Aybert (FR)

(73) Assignee: AURIGA INTERNATIONAL, Waterloo (BE)

( * ) Notice: Subject to any disclaimer, the term of this patent is extended or adjusted under 35 U.S.C. 154(b) by 97 days.

(21) Appl. No.: 13/811,619

(22) PCT Filed: Jul. 19, 2011

(86) PCT No.: PCT/EP2011/062329
§ 371 (c)(1),
(2), (4) Date: Feb. 14, 2013

(87) PCT Pub. No.: WO2012/010587
PCT Pub. Date: Jan. 26, 2012

(65) Prior Publication Data
US 2013/0143963 A1    Jun. 6, 2013

(30) Foreign Application Priority Data
Jul. 23, 2010  (BE) .................................. 2010/0462

(51) Int. Cl.
| A61K 47/34 | (2006.01) |
| A61K 9/107 | (2006.01) |
| A61K 47/14 | (2006.01) |
| A61K 47/22 | (2006.01) |
| A61K 47/24 | (2006.01) |

(52) U.S. Cl.
CPC ............... *A61K 47/34* (2013.01); *A61K 9/1075* (2013.01); *A61K 47/14* (2013.01); *A61K 47/22* (2013.01); *A61K 47/24* (2013.01)

(58) Field of Classification Search
USPC ........................................................ 514/514
See application file for complete search history.

(56) References Cited

U.S. PATENT DOCUMENTS
| 5,411,986 | A |  | 5/1995 | Cho et al. |
| 2003/0091518 | A1 | * | 5/2003 | Pauly et al. ........................ 424/59 |
| 2006/0127996 | A1 | * | 6/2006 | Fahey ................................ 435/128 |
| 2008/0176942 | A1 |  | 7/2008 | Dagan et al. |

FOREIGN PATENT DOCUMENTS
| EP | 2163236 | 3/2010 |
| FR | 2804318 | 8/2001 |
| FR | 2820035 | 8/2002 |
| FR | 2888235 | 1/2007 |
| WO | 0215722 | 2/2002 |
| WO | 2008007728 | 1/2008 |

OTHER PUBLICATIONS

Derwent Abstract of EP 2 163 238 A2. Original Document Publication Date: Mar. 17, 2010.*
European Patent Office International Search Report dated Oct. 24, 2011, for International Application No. PCT/EP2011/062329, Applicant, Auriga International (6 pages).

* cited by examiner

*Primary Examiner* — Sreeni Padmanabhan
*Assistant Examiner* — Jody Karol
(74) *Attorney, Agent, or Firm* — Koppel, Patrick, Heybl & Philpott

(57) ABSTRACT

A stable galenic composition of a compound of general formula (I) wherein $R_1$ and $R_2$ both represent independently of each other an alkyl, aryl, arylalkyl group, optionally substituted with one or more linear or branched groups, optionally bearing one or more heteroatoms,

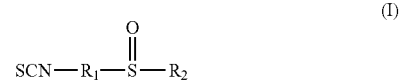

comprising said compound of formula I in an amount ranging from 0.01 to 15% by weight based on the total weight of the final composition; at least one anhydrous ester, the main chain and/or optionally the branched chains of which are free from free and/or reactive groups or functions, in an amount ranging from 0.1 to 99.9% by weight based on the total weight of the cosmetically and pharmaceutically acceptable composition; and optionally a cosmetically and pharmaceutically acceptable excipient for completing the 100% of the total weight of the composition.

10 Claims, 10 Drawing Sheets

SULFORAPHANE STABILIZATION

The present invention relates to the field of the stabilization of a compound of general formula (I) wherein $R_1$ and $R_2$ both represent independently of each other an alkyl, aryl, arylalkyl group, linear or branched, optionally substituted with one or more heteroatoms,

More particularly, the present invention relates to the stabilization of a compound of general formula (I) wherein $R_1$ represents a butyl group and $R_2$ represents a methyl group, said compound of general formula (I) being sulforaphane.

From the literature, it is known that sulforaphane is unstable to heat in the presence of water and keeping it at $-20°$ C. is generally recommended.

Moreover, the injection of sulforaphane (I) in gas chromatography shows that 80% of the product is degraded into 3-butenylisothiocyanate (4) according to the reaction (I).

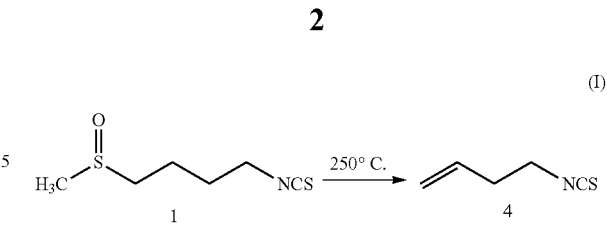

It has been demonstrated that this product specifically stems from thermal degradation of sulforaphane in the thermostated injector at 250° C. of gas phase chromatography (see FIG. 1, A). Indeed, when the sample is directly injected onto the column without passing through the injector, no degradation peak is observed (see FIG. 1, B).

In addition to the formation of 3-butenylisothiocyanate 4, mentioned above, various other volatile degradation products were identified, during the heating of sulforaphane in water, such as dimethyl disulfide 5, S-methyl methylthiosulfinate 6, S-methyl methylthiosulfonate 7, methyl (methylthio)methyl disulfide 8, 1,2,4-trithiolane 9 and 4-isothiocyanato-1-(methylthio)-1-butene 10 according to the reaction (II).

These volatile products are formed via a radical route generating methylthio 12 and methylthiosulfinyl 13 radicals as well as through various intermolecular reactions involving the sulfoxide function and passing through the intermediate 11.

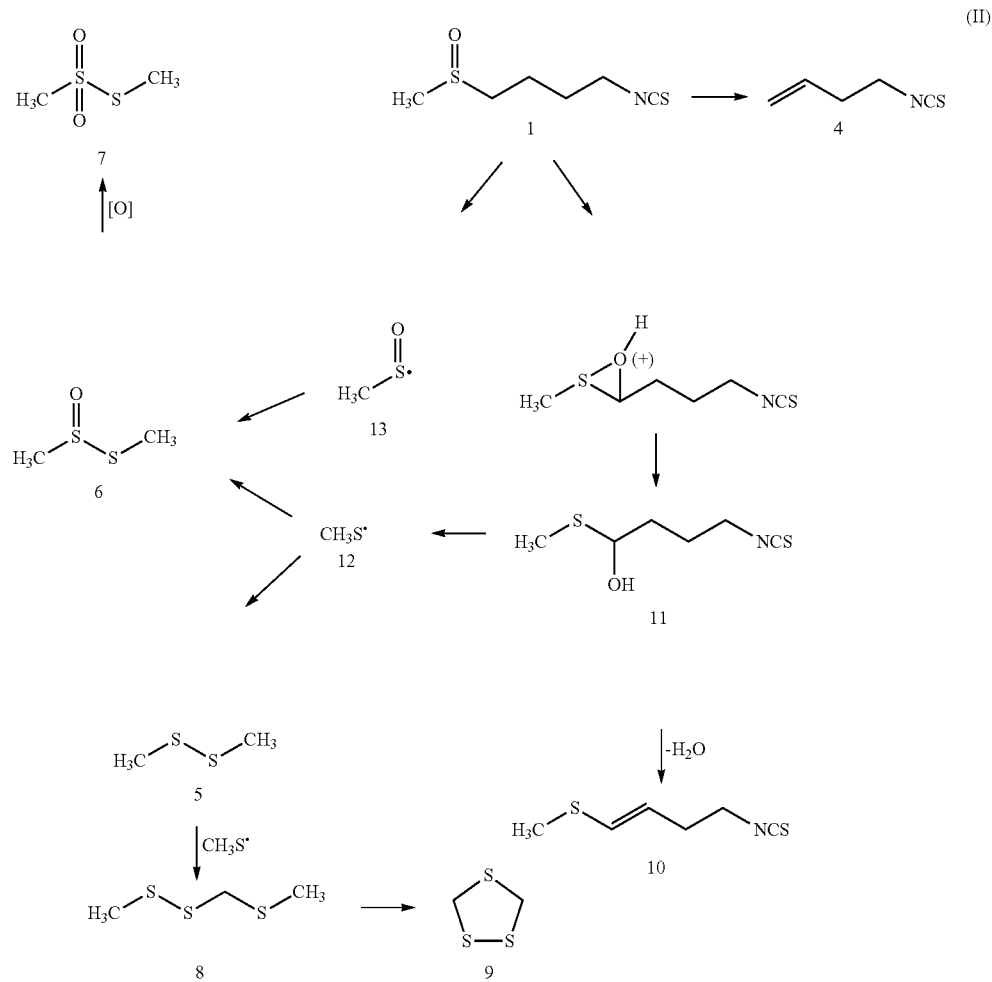

A single main non-volatile product was isolated and identified as being the coupling product of the amine generated during hydrolysis of sulforaphane on residual sulforaphane: N,N'-di-(4-methylsulfinyl)butyl thiourea 14. The formation of this product indeed results from the reaction of sulforaphane 1 with 4-methylsufinyl butylamine 15 itself generated by hydrolysis of sulforaphane 1 according to the reaction (III)

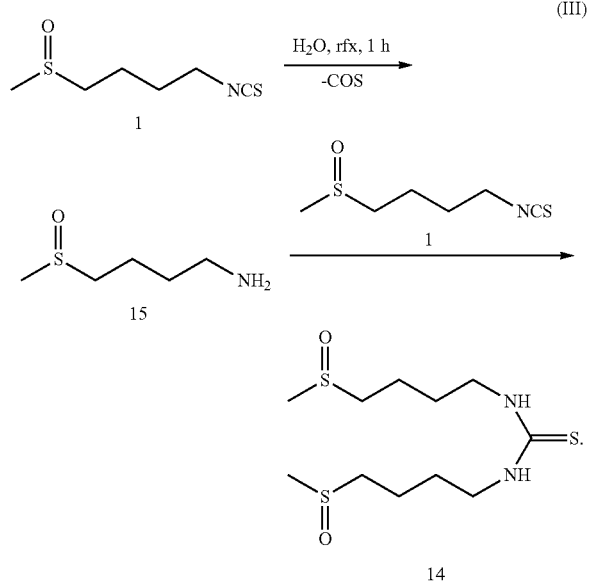

Therefore there exists a need for finding one or more agents for stabilizing sulforaphane.

Document FR 2888235 discloses a method with which sulforaphane may be stabilized by means of acacia gum. This document discloses that sulforaphane is sensitive to light, to oxygen and to temperature for the extracted concentrated product.

Acacia gum or gum arabic has film-forming properties which allow protection of an active ingredient by forming a barrier to oxygen, to light and to water by matrix encapsulation.

A natural sample of sulforaphane was stabilized with different acacia gum contents. In document FR 2888235, samples containing 50% and 70% of acacia gum, i.e, respective sulforaphane contents of 36.05% and 22.4% are placed under normal ageing (25° C. and 60% of humidity) and accelerated conditions (40° C. and 75% of humidity). Sulforaphane is assayed over several weeks, thereby allowing determination of the degradation percentage of the product.

Unfortunately, in this document, the sample having 50% of acacia gum does not exhibit any particular stabilization and under accelerated ageing conditions, the degradation is twice more significant than under normal conditions. The sample having 70% gum arabic content also shows a degradation under both ageing conditions but to a lesser extent than the previous sample. Indeed, the degradation does not exceed 30% after one month and 40° C. while at 25° C., slight degradation is observed the first week, and then the sulforaphane extract seems to be relatively stable and does not show any increase in the degradation percentage. Further, such an amount of stabilizer does not leave any room for other compounds in the making of formulations.

Document EP 2120969 also discloses a method with which sulforaphane may be stabilized, which is known in the form of an unstable oil by using cyclodextrins. This document does not disclose the origin of the instability of sulforaphane and even proposes to dilute it before putting it into contact with a cyclodextrin.

Cyclodextrins are oligosaccharides consisting of 5 (or more) α-D-glucopyranosucide units bound in 1-4 and capable of forming complexes by inclusion of hydrophobic molecules. The latter may be released under certain conditions by insertion of another molecule into the cyclodextrin.

According to EP 2120969, three different cyclodextrins were used: α, β and γ cyclodextrins which respectively consist of 6, 7 and 8 sugar molecules. The amount of sulforaphane was determined by HPLC by using an internal standard after having placed the sulforaphane-cyclodextrins complexes under different conditions: sealed samples stored at room temperature or at −30° C. and open sample packaged at 40° C.

The result of this investigation is that the α-cyclodextrins are more stabilizing and allow sulforaphane to be kept with a degradation of less than 10% after seven months, while with less suitable and not very stabilizing cyclodextrins up to 50% of degradation are observed after this same period of time.

Unfortunately, the selection of the cyclodextrin remains complicated and does not allow sulforaphane to be applied in a sunscreen.

In order to produce a cosmetic galenic preparation, an adequate medium has to be found for diluting the active substance in order to attain the active substance concentration per unit surface of the skin. In selecting this diluent medium, one skilled in the art generally selects an aqueous phase, an alcohol or a mixture of the latter (the other organic solvents being generally inapplicable on the skin).

On this subject, document EP 2163238 discloses a very long list of carboxylic acids mixed with sulforaphane or certain derivatives such as for example sulforaphene in order to obtain a depigmenting action.

Document WO 02/15722 discloses a method for avoiding the growth of *Helicobacter* through the use of glucosinolate, of a isothiocyanate or of one of its derivatives. The isothiocyanate may be sulforaphane and the disclosed treatment method involves administration of compositions to patients.

This document also teaches food products added with their compositions containing glucosinolates, isothiocyanates.

On page 12 of this document, a lot of excipients or carriers for such compositions are disclosed, among which are found water, solutions, dispersions, suspensions, aqueous or non-aqueous emulsions, sterile powders to be regenerated. This document discloses as examples of carriers, diluents, solvents or aqueous or non-aqueous excipients, water, ethanol, polyols, carboxymethylcellulose, vegetable oils and injectable organic esters such as an ethyl oleate.

Finally, a lot of adjuvants are mentioned such as preservatives, wetting agents, emulsifiers or dispersants and anti-bacterial, anti-fungic agents (parabene, chlorobutanol, phenol, ascorbic acid, . . . ) binders, powdering particles such as fillers, adsorption-delaying agents, . . . .

Document WO2008/007728 discloses a preparation of coenzyme A in a lipid structure according to the title of the application. A detailed analysis of the document reveals that this document discloses skin care preparations for external use, the whitening effect of which on the skin is improved.

This preparation comprises a hydroquinone glycoside or one of these derivatives as a whitening agent, L-ascorbic acid, a placenta extract, an alkyl resorcinol, a tranexamic acid and a coenzyme A. This document discloses that whitening agents of the kojic acid, colloidal sulfur and hydroquinone type are degraded in pharmaceutical preparations and their effect is lost.

The object of this document is the addition of an oxidizing coenzyme A in order to improve the effect of the whitening agent in a skin whitening care product. This document uses liposomes as a carrier for the whitening agent. However, this document does not mention sulforaphane.

Document FR 2804318 discloses formulations containing water and glucoraphene or sulforaphane as well as an anti-UV/IR protection factor and/or antioxidants.

Among the mentioned protection factors, are found in bulk for the UVB filters, camphors, benzoic, cinnamic, salicylic acid esters, benzophenone derivatives, benzalmalonic acid esters, derivatives of triazines or further a few ketones and alkanes. Sulfonic acids and their salts are further found. For the UVA filters, are further found benzoylmethane derivatives, enamine compounds, finally photoprotective pigments may also be added such as metal oxides or their salts (ZnO, $TiO_2$, FeO, $Fe_2O_3$, . . . ), silicates, sulfates or stearates.

Further, as antioxidants, called secondary photo-protective agents, are further found a great many amino acids, imidazoles, peptides, carotenes or carotenoids, chlorogenic acid, lipoic acid, propylthiouracil, glutathione, glycosyl, N-acetyl, methyl, ethyl esters etc.

Unfortunately, preparing a dilution of sulforaphane in an aqueous phase, an alcohol or a mixture of the latter has proved to be disastrous as for the stability of the sulforaphane.

Indeed, it was shown according to the invention and surprisingly that sulforaphane, contrary to what is most commonly suggested, is not sensitive to light, to oxidants, etc., under normal conditions of use. The major problem is in fact essentially due to its capability of reacting with nucleophilic agents when it is placed in solution, without any actual influence of the previous parameters.

Even if it was known that sulforaphane has instability in an aqueous phase at 50° C. and at 100° C. in the open air, it was not possible to know whether the instability was due to the temperature or to the aqueous phase or further to the oxidation, since few serious investigations were available concerning this instability. Moreover, document EP 2163238 therefore describes a set of formulations which are oil-in-water emulsions (therefore essentially consisting of water) and it is known that water is a degradation factor of sulforaphane since it is a nucleophilic agent.

Further, certain formulations according to EP 2163238 further contain an alcohol, 1,6-hexanediol, which is also nucleophilic. This document therefore discloses formulations which cannot be stable and which contain after storage many degradation products. Moreover, no information as to the stabilization of sulforaphane is mentioned in this document, nor as to the degradation of the active substance.

As for document WO 02/15722, it also mentions many components of various disclosed bulk compositions and without any specifications, which are in majority based on water or are alcohols. In the examples, sulforaphane or broccoli extracts containing it are diluted in the culture medium or in a foodstuff. The media are all of an aqueous, hydrophilic and polar nature, which is detrimental to the stability of sulforaphane and rapidly produces degradation products.

Document WO 2008/007728 therefore discloses that whitening agents of the Logic acid, hydroquinone or colloidal sulfur type are degraded in pharmaceutical preparations and therefore proposes the use of liposomes. Now, it has been shown according to the invention that liposomes do not allow stabilization of sulforaphane (see comparative example 1).

Finally document FR 2888235 therefore discloses galenic compositions for external use comprising a wide range of additives and always water. Consequently if the active agent is glucoraphanine it will remain stable, but if it is sulforaphane, it will degrade into a thiourea. (Let us note that in reality, glucoraphanine, if it is more stable, it is inactive). This document therefore does not disclose any solution for stabilizing sulforaphane in a galenic composition.

Therefore there exists a need for providing a stable sulforaphane composition which allows provision of a stable cosmetic or pharmaceutical composition which is industrially viable.

In order to solve this problem, the invention therefore provides a stable galenic composition of a compound of general formula I wherein $R_1$ and $R_2$ both represent independently of each other, an alkyl, aryl, arylalkyl group optionally substituted with one or more linear or branched, optionally cyclic, groups, optionally bearing one or more heteroatoms.

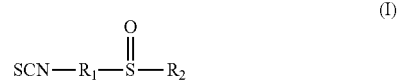

(I)

comprising said compound of formula I in an amount ranging from 0.01 to 15% and preferably between 0.1 and 4%, more particularly between 0.1 and 2% by weight based on the total weight of the final composition, at least one anhydrous ester, the main chain and/or optionally the branched chains of which are free from free and/or reactive groups or functions, in an amount ranging from 0.1 to 99.9% by weight based on the total weight of the cosmetically and pharmaceutically acceptable composition, and optionally a cosmetically and pharmaceutically acceptable excipient for completing the 100% of the total weight of the composition.

By the terms of "at least one anhydrous ester, the main chain and/or optionally the branched chains of which are free from free and/or reactive groups or functions", is meant in the sense of the present invention, esters with an identified or identifiable chemical structure neither including on its side chain(s), nor on its main chain any free and reactive functional groups or functions, i.e. groups or functions which are neither complexed, nor protected whether chemically or sterically.

Such esters are therefore compatible with the active molecule and are for example i.a. free from nucleophilic groups. Such anhydrous esters free from free and/or reactive groups or functions are also esters such that the synthesis or extraction process does not induce the presence in the finished product of other molecules incompatible with the active substance. Of course, in the sense of the invention, the wording "at least one anhydrous ester, the main chain and/or optionally branched chains of which are free from free and/or reactive groups or functions" also covers a mixture of esters each corresponding to the previous definition, but excludes any mixture or optional natural extract which may be described as rich in ester or in a mixture of esters but containing a set of other molecules.

In this way, the composition according to the invention may equally be a stabilized additive based on a stable compound of formula (I) and be non-degraded over time in an anhydride ester with chains free from free and/or reactive groups or functions as a carrier or a cosmetic or pharmaceutical formulation in which an additional excipient is present.

This cosmetic and pharmaceutically acceptable excipient should be of the non-aqueous, non-nucleophilic, non-hygroscopic, non-hydrated type. More particularly, this cosmetic and pharmaceutical excipient cannot be an ester which does not fit the previous definition, should be non-hygroscopic, non-hydrated, cannot be a surfactant for the purpose of forming emulsions of the aqueous phase/oily phase type, cannot include free and/or reactive functions in the sense of what was defined above for example (SH, $NH_2$, $NH_3^+$) whichever the position on the side or main chain in order not to be capable of degrading sulforaphane and therefore capable of improving the efficiency of the composition.

With the small group of anhydrous esters, the chains of which are free from free and/or reactive groups or functions, which may therefore be used, it is possible to avoid any contact with nucleophilic functions which degrade the compound of formula (I), which was demonstrated by the present invention and this, contrary to expectation when considering the prior teachings which either bluntly teach an excipient with a nucleophilic agent or teach an instability due to amounts of exterior elements without actually indicating the source of degradation of sulforaphane.

Preferably, said compound of general formula (I) is sulforaphane, i.e. $R_1$ represents a butyl group and $R_2$ a methyl group.

Indeed, following the investigation demonstrating the stability problem of sulforaphane in an aqueous phase, an alcohol or a mixture of the latter, it was shown that the compound of general formula (I) was essentially sensitive to degradation because of its isothiocyanate function accessible to the nucleophilic agents and it emerges, in spite of the many studies of efficiency conducted on sulforaphane up to now, that the development seemed to be limited by the problem of the cost of the raw material, its availability and its instability.

Advantageously, said cosmetically and pharmaceutically acceptable anhydrous ester is selected from the group consisting of acetates, benzoates, salicylates, ester 610, caprylic/capric/succinic triglycerides, stearates and isostearates, ethyl hexanoates, palmitates, isononanoates, oleates, neopentanoates, myristates and the like, the chains of which are free from free and/or reactive groups or functions.

In an advantageous embodiment according to the invention, sulforaphane is natural extracted or synthetic sulforaphane. Synthetic sulforaphane is more accessible as regards amount and purity. The sulforaphane used may be racemic or optically pure.

Advantageously said cosmetically and/or pharmaceutically acceptable excipient is a methylpolysiloxane.

In a preferential embodiment, said composition is a galenic composition such as a sunscreen product, a product against hyperpigmentation, a depigmenting product, an anti-pollution screen, a treatment product against lucite, cancer (of the skin) and the like, such as for example a protective agent against the effects of radiations.

The anhydrous esters with chains free from free and/or reactive groups of functions of the composition according to the invention are typically highly stable hydrating and healing esters which do not become stale, which form a good penetrating agent and regulate the production of sebum.

As this was already mentioned, there exists little specific information on the long term stability since the degradation phases are slow at room temperature, except in the presence of nucleophilic agents: this poses the most problems for a galenic formulation (notably a topical formulation).

Further, in a commercial preparation, the compound of general formula (I) seems to have to be more protected against nucleophilic agents than against oxidation "in air".

At the present time, there is a need for obtaining a stable galenic composition of the compound of the general formula in a novel type of cosmetic or pharmaceutical preparation in order to replace those which usually contain nucleophilic agents.

For this purpose, the stability of the particular sulforaphane compound was investigated under different conditions of solubilization and of temperatures. With HPLC tracking, it was possible to determine the amount of residual sulforaphane over time. Various degradation products were also identified.

This investigation allowed confirmation that sulforaphane is very sensitive to nucleophilic agents which degrade it rapidly by acting on the isothiocyanate function.

Other embodiments of the composition according to the invention are mentioned in the appended claims.

The invention also relates to a method for stabilizing a compound of general formula (I) wherein $R_1$ and $R_2$ both represent independently of each other, an alkyl, aryl, alrylalkyl group optionally substituted with one or more linear or branched, optionally cyclic, groups optionally bearing one or more heteroatoms,

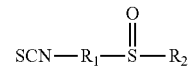

(I)

comprising a step for mixing said compound of general formula (I) with a cosmetically and pharmaceutically acceptable anhydrous ester with chains free from free and/or reactive groups or functions, and a step for forming a stable composition towards degradation by nucleophilic functions.

Advantageously, said anhydrous ester with chains free from free and/or reactive groups or functions is selected from the group consisting of acetates, benzoates, salicylates, ester 610, caprylic/capric/succinic triglycerides, stearates and isostearates, ethyl hexanoates, palmitates, isononanoates, oleates, neopentanoates, myristates and the like.

In particular, said ester is selected from acetates (benzyl, linalyl, tocopheryl acetate, ...), benzoates (benzyl benzoate, alkyl benzoate, ...) salicylates (benzyl, methyl, ethyl, amyl salicylates, ...), ester 610, caprylic/capric/succinic triglycerides, stearates and isostearates (isostearyl isostearate, cetearyl stearate, ...), ethyl hexanoate, palmitates, (octyl palmitate, ...), isononanoates, oleates, neopentanoates (isostearyl neopentanoate ...), myristates, ....

Preferably, the sulforaphane is a natural extracted or synthetic sulforaphane.

In a preferred embodiment according to the invention, the method further comprises a step for mixing said compound of general formula (I) stabilized with at least one cosmetically and pharmaceutically acceptable excipient.

Advantageously, said excipient is selected from the group of methylpolysiloxanes and their derivatives, preferably in liquid, oily, gel, cream form, ....

Other embodiments of the method according to the invention are indicated in the appended claims.

The present invention also relates to the use of a cosmetically and pharmaceutically acceptable anhydrous ester with chains free from free and/or reactive groups or functions, for stabilizing a compound of general formula (I) wherein $R_1$ and $R_2$ both represent independently of each other an alkyl, aryl, arylalkyl group, optionally substituted with one or more linear or branched, optionally cyclic, groups optionally bearing one or more heteroatoms,

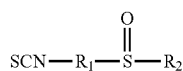

(I)

in a galenic formulation typically a sunscreen product, a product against hyperpigmentation, a depigmenting product, an anti-pollution screen, a product against lucite, cancers (of the skin) and the like.

More particularly, said anhydrous ester, the chains of which are free from free and/or reactive groups and functions, is selected from the group consisting of acetates, benzoates, salicylates, ester 610, caprylic/capric/succinic triglycerides, stearates and isostearates, ethyl hexanoates, palmitates, isononanoates, oleates, neopentanoates, myristates and the like.

Other forms of use according to the invention are mentioned in the appended claims.

Other characteristics, details and advantages of the invention will become apparent from the description given hereafter, not as a limitation and referring to the appended examples and to the figures.

The stability of sulforaphane was investigated in the following way: a 1% sulforaphane solution is prepared in different media to be tested. The preparation, maintained in a closed container is then thermostated at 25° C., 37° C. or 40° C. Kinetic tracking is carried out by assaying the residual sulforaphane.

The HPLC method used is the following:
Column: Discovery C18 (15 cm×4.8 mm×5 μm)
Mobile Phase: isocratic $CH_3CN/H_2O$ (50/50)
Flow Rate: 1 mL/min.
$\lambda = 245$ nm
Injection (10 μL) after dilution of the parent solution in the mobile phase in order to obtain a sulforaphane concentration of 1 mg/mL.
External standard: naphthalene.

a) Stability in water

Figure 1:
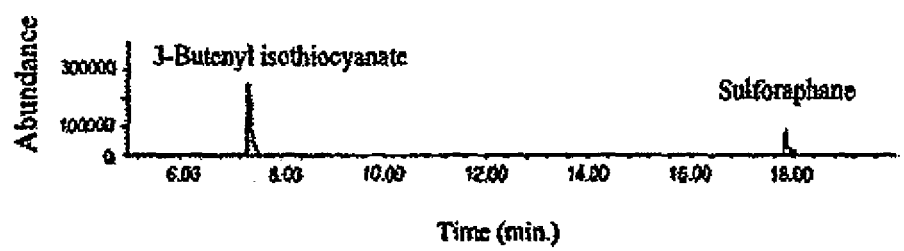
FIG. 1 illustrates the degradation of sulforaphane at 250° C.
Figure 1:
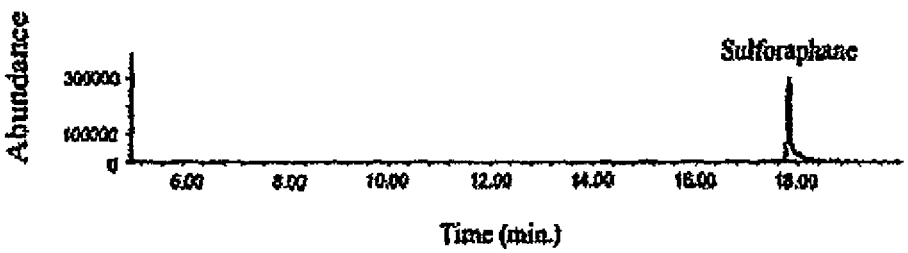
Figure 2:
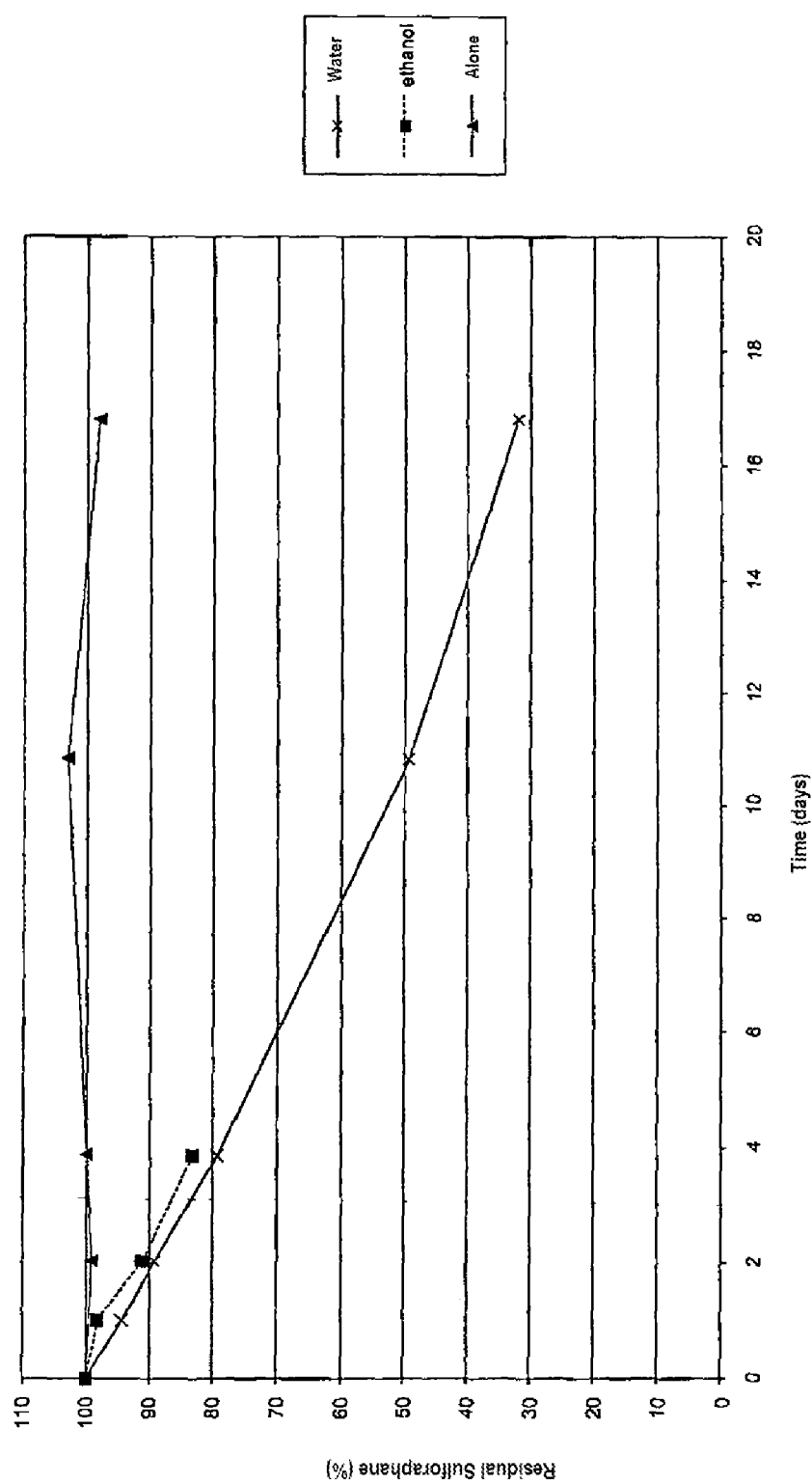
FIG. 2 illustrates the stability of sulforaphane alone in water and in alcohol at 40° C.

Chromatography of the stability test samples at 40° C. reveals with UVs, a loss of 10% after only 2 days. At the beginning of the stability tests, we do not observe any new peak, which is explained by the formation of the amine which is not detected with this method. Next, a peak appears which corresponds to the formation of thiourea. The results of the residual contents over time are plotted as a graph in FIG. 2. The chromatogram is not illustrated. After 10 days, there remains only 50% of the initial content.

b) Stability in ethanol

Chromatographic analysis (not shown) reveals that as soon as the first day, a second peak close to the one of sulforaphane already appears, which we identified as the coupling compound with ethanol. Degradation in ethanol at 40° C. is tracked for a shorter period of time since the very strong difference in absorbance, as well as the similarity of the retention times between sulforaphane and the coupling derivative is detrimental to the quality of the analysis at the longest times. Nevertheless, the trend is already very dearly marked as soon as the early days. The results of the residual sulforaphane content are plotted on the graph in FIG. 2.

c) Stability in an "antioxidant" medium in solution in a hydro-alcoholic medium.

Figure 3:
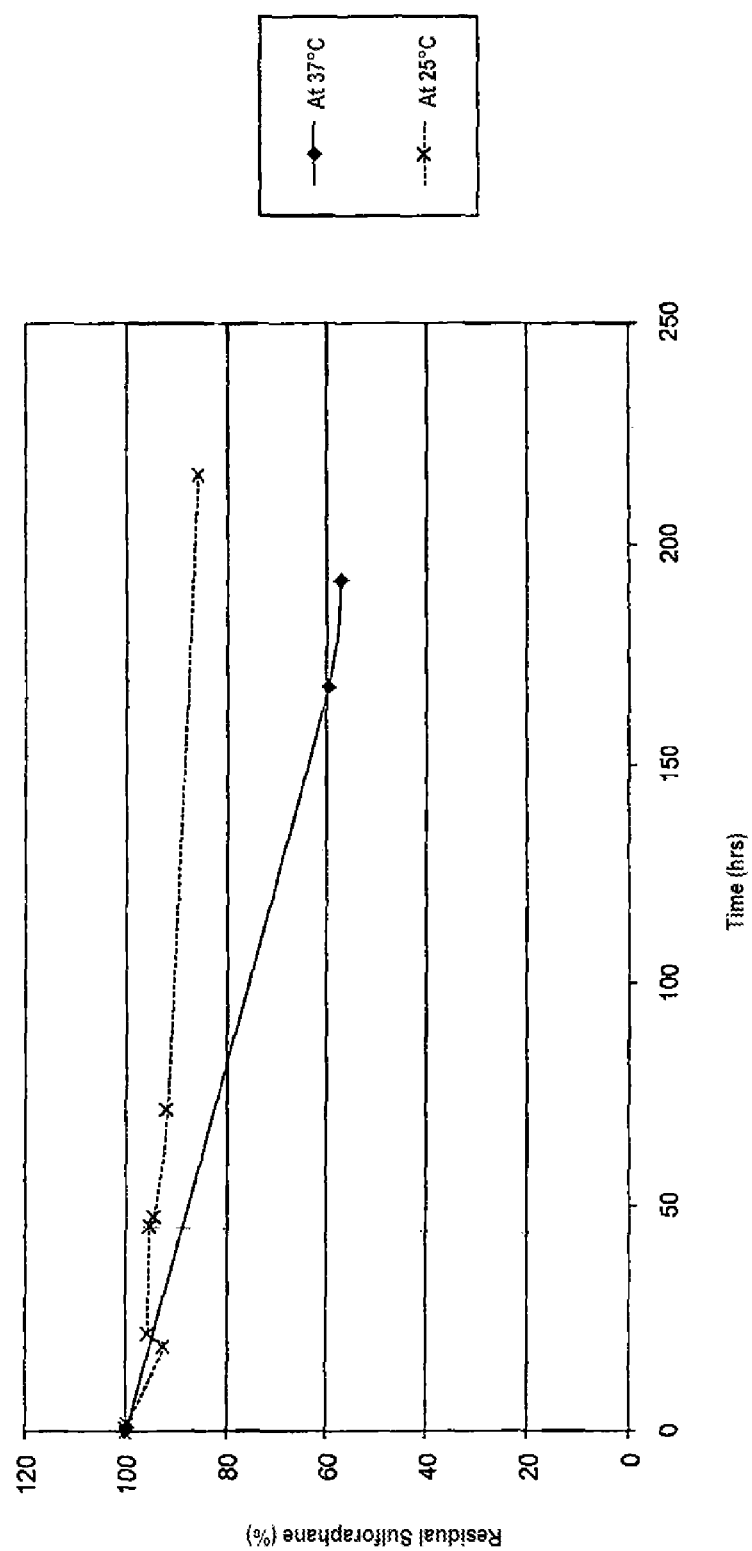
FIG. 3 illustrates the stability in a hydro-alcoholic antioxidant medium versus temperature.

As this may be seen in FIG. 3, the amount of residual sulforaphane begins to fall after 1 day at 25° C. At 37° C., in less than 7 days, there remains no more than 50% of the initial amount.

It clearly appears here that the sulforaphane cannot be recovered in a commercial preparation which would use an alcohol or water as a solvent, and this even in the presence of antioxidants, which once again confirms that the instability is essentially due to nucleophilic agents and not to oxidants.

Indeed, in an aqueous medium, degradation of sulforaphane generates the amine (precursor of sulforaphane). The latter will react on the residual sulforaphane and form the corresponding thiourea according to reaction IV.

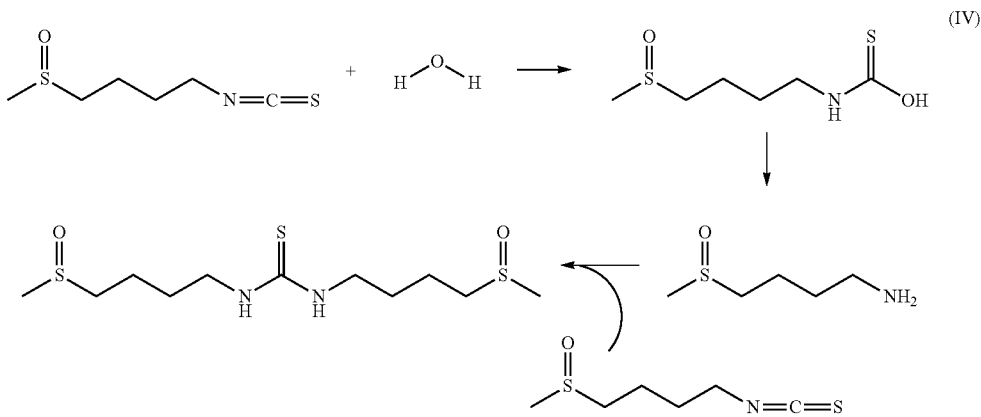

(IV)

In an alcoholic medium (as in the presence of thiols), the intermediate formed is more stable and the reaction stops, as shown below in reaction V in the case of an alcohol.

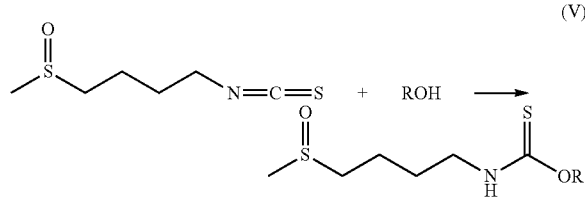

(V)

The stability of sulforaphane was then investigated in organic solvents.

Stability tests on sulforaphane in solution in solvents which cannot be used in cosmetics but are assumed to be inert towards this molecule were conducted with NMR tracking. We were thus able to show that sulforaphane remains stable for at least one week when it is kept in a closed flask, but non-inertized and exposed to light in solution in DMSO or in chloroform.

24 hour heating with reflux of a sulforaphane solution in chloroform did not either show any degradation (by NMR).

Since the sulforaphane contains an isothiocyanate function, and that allyl isothiocyanate is known for generating degradation products similar to those observed for sulforaphane, the stabilization of allyl isothiocyanate was investigated.

Indeed, thermal degradation of allyl isothiocyanate was investigated after heating for one hour in boiling water. The degradation leads to the formation of diallyl thiourea according to the reaction VI.

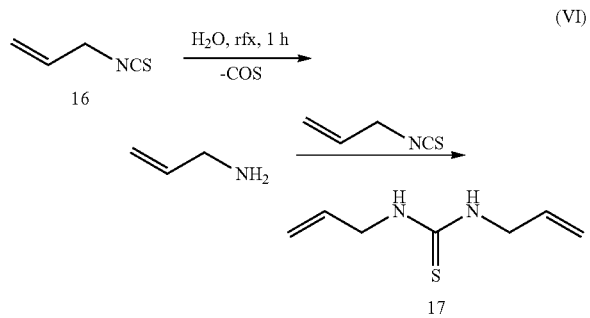

(VI)

This is similar to what is observed for sulforaphane (formation of thiourea).

The best thermal stability of isothiocyanates in an acid medium has already been reported in the case of allyl isothiocyanate. Indeed, during treatment of the sample for one hour in boiling water, the concentrations of degradation products increase with pH.

The results are shown in the table.

| Entry | Degradation product | Concentration at pH 2.7 (mg/g) | Concentration at pH 7.0 (mg/g) | Concentration at pH 9.0 (mg/g) |
|---|---|---|---|---|
| 1 | diallyl sulfide | 13.09 | 22.16 | 26.40 |
| 2 | allyl isothiocyanate | 379.06 | 290.27 | 270.46 |
| 3 | allyl thiocyanate | 9.21 | 13.84 | 12.32 |

-continued

| Entry | Degradation product | Concentration at pH 2.7 (mg/g) | Concentration at pH 7.0 (mg/g) | Concentration at pH 9.0 (mg/g) |
|---|---|---|---|---|
| 4 | diallyl disulfide | 8.09 | 11.47 | 12.71 |
| 5 | 3H-1,2-dithiolene | 0.13 | 0.17 | 0.19 |
| 6 | diallyl trisulfide | 10.31 | 13.63 | 14.11 |
| 7 | 2-vinyl-4-1,3-dithiin | Traces | Traces | Traces |
| 8 | 4H-1,2,3-trithiin | Traces | Traces | Traces |
| 9 | 5-methyl-1,2,3,4-tetrathiane | 0.01 | 0.02 | 0.03 |
| 10 | diallyl tetrasulfide | Traces | Traces | Traces |

The commercial allyl isothiocyanate is for example sold in a stabilized form by Sigma-Aldrich by means of Ionol (2,6-dit-tert butyl-4-methylphenol) known for its antioxidant properties.

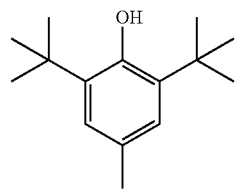 [SMILES: Cc1cc(C(C)(C)C)c(O)c(C(C)(C)C)c1]

Further, it is also known how to stabilize allyl isothiocyanate with ascorbic acid. We were able to observe that ascorbic acid added at 0.1% by weight has a marked effect on the stability of allyl isothiocyanate upon storage at 37° C. for 16 weeks. Ascorbic acid does not affect the color of the horseradish powder (wasabi) containing isothiocyanate and when this powder is mixed with water, ascorbic acid also shows a stabilizing effect on allyl isiothiocyanate as well as on its color.

A similar study with sulforaphane showed that the ascorbic acid was not able to stabilize sulforaphane while it is acid and antioxidant on the one hand.

As this may be seen, unlike what has been published, light or oxygen do not promote the degradation of sulforaphane and are not the most problematic factors. It is actually the use of media containing nucleophilic agents such as alcohols or water, currently used in cosmetics or galenics which should be banned and replaced.

It was therefore concluded form the foregoing that the nucleophilic functions are the ones which cause degradation of sulforaphane.

Various potentially stabilizing matrices were then tested:

COMPARATIVE EXAMPLE 1

Stabilization of Sulforaphane with Phospholipids

Phospholipides do not have any nucleophilic function as such and form a matrix sometimes used in cosmetic products.

1% of sulforaphane were placed per mL of solution containing diphospholipides such as for example Phosal®. The preparation, maintained in a closed container is then thermostated at 40° C. Kinetic tracking is carried out by assaying the residual sulforaphane:

The HPLC method used is the following:
Column: Discovery C18 (15 cm×4.6 mm×5 μm)
Mobile Phase: isocratic $CH_3CN/H_2O$ (50/50)
Flow Rate: 1 mL/min.
λ=245 nm
Injection (10 μL) after dilution of the parent solution in the mobile phase in order to obtain a sulforaphane concentration of 1 mg/mL.
External standard: naphthalene.

Figure 4:
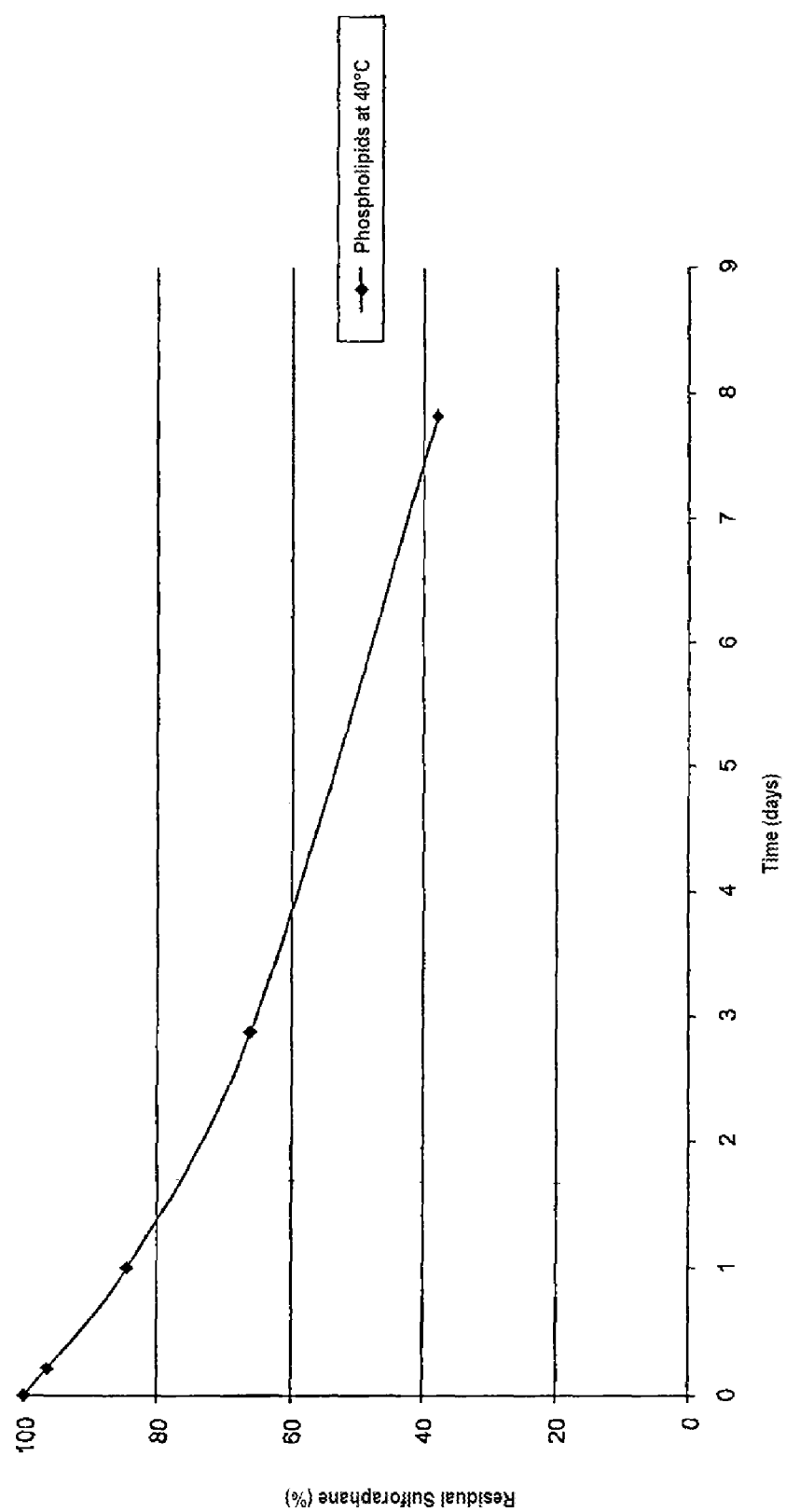
FIG. 4 illustrates the stability of sulforaphane in a medium containing phospholipids.

As this may be seen in FIG. 4, degradation is very fast here, more than 40% degradation in less than 3 days.

In the case of phospholipids, this product in fact contains a certain amount of ethanol. This may explain the rapid formation of a compound which we have demonstrated to be the coupling product between ethanol and sulforaphane isothiocyanate. However degradation is faster here than in ethanol alone.

COMPARATIVE EXAMPLE 2

Stabilization of Sulforaphane in Various Vegetable Oils

Figure 5:
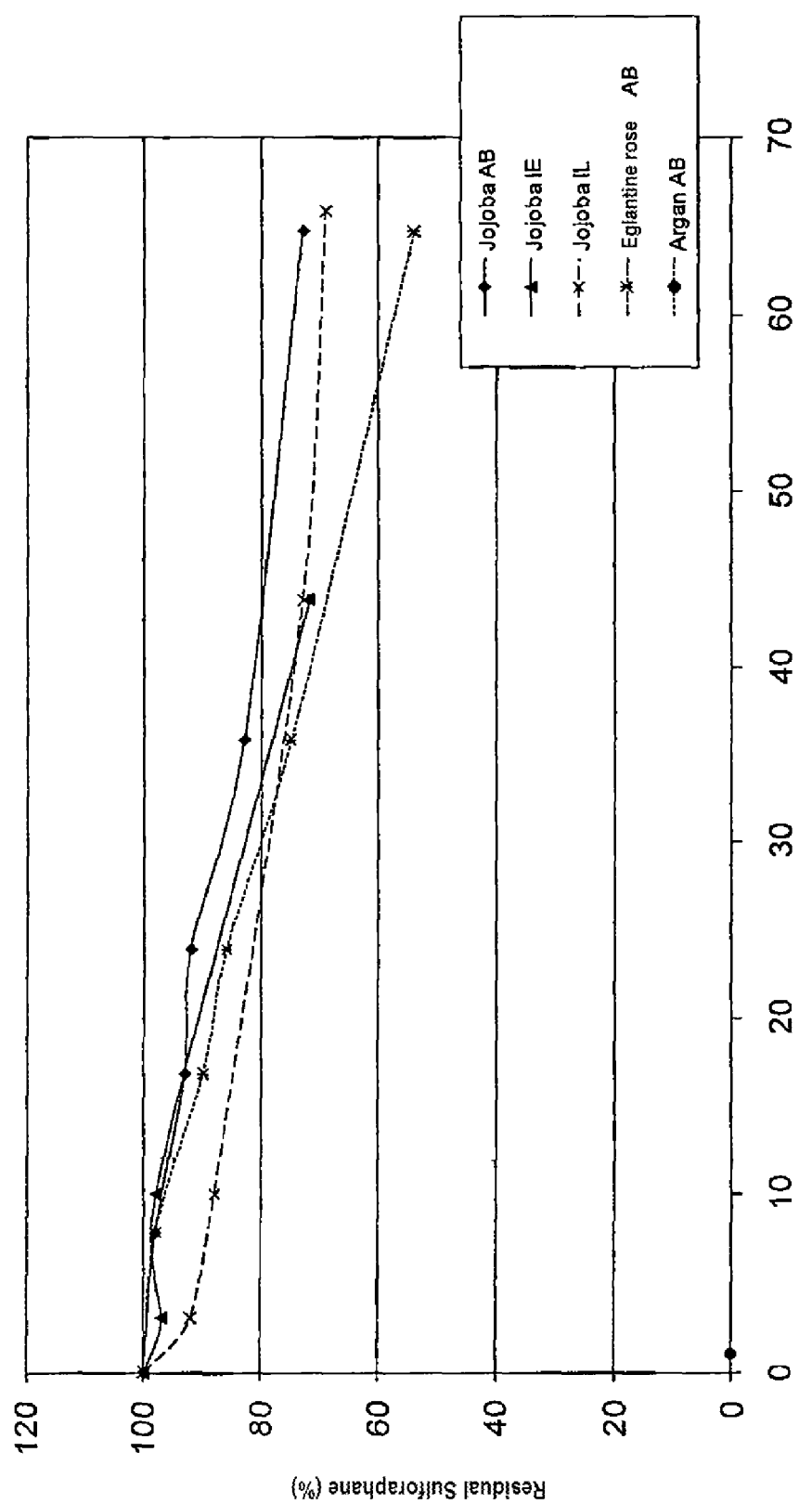
FIG. 5 illustrates the stability of sulforaphane in different vegetable oils free from nucleophilic fatty alcohol or function.

Jojoba oil contains derivatives of mono-unsaturated fatty acids free from fatty alcohols. 1% (m/m) sulforaphane solutions were prepared in jojoba, argan and eglantine rose oils (plant extract). Kinetic tracking of the degradation was then carried out by using as an external standard naphthalene like above. As this may be seen in FIG. 5, the potential stabilization is rather disappointing, although degradation is slower than in the previous media. Further, solubility of sulforaphane in the oils is limited, about 0.5% (m/m) in jojoba oil, 2% in argan oil and 3.5% in eglantine rose oil. Further, the observed degradation (see FIG. 5) remains too substantial to allow commercial use. Further, since these are complex natural products, there exists variability in quality between providers and between batches.

COMPARATIVE EXAMPLE 3

Figure 10:
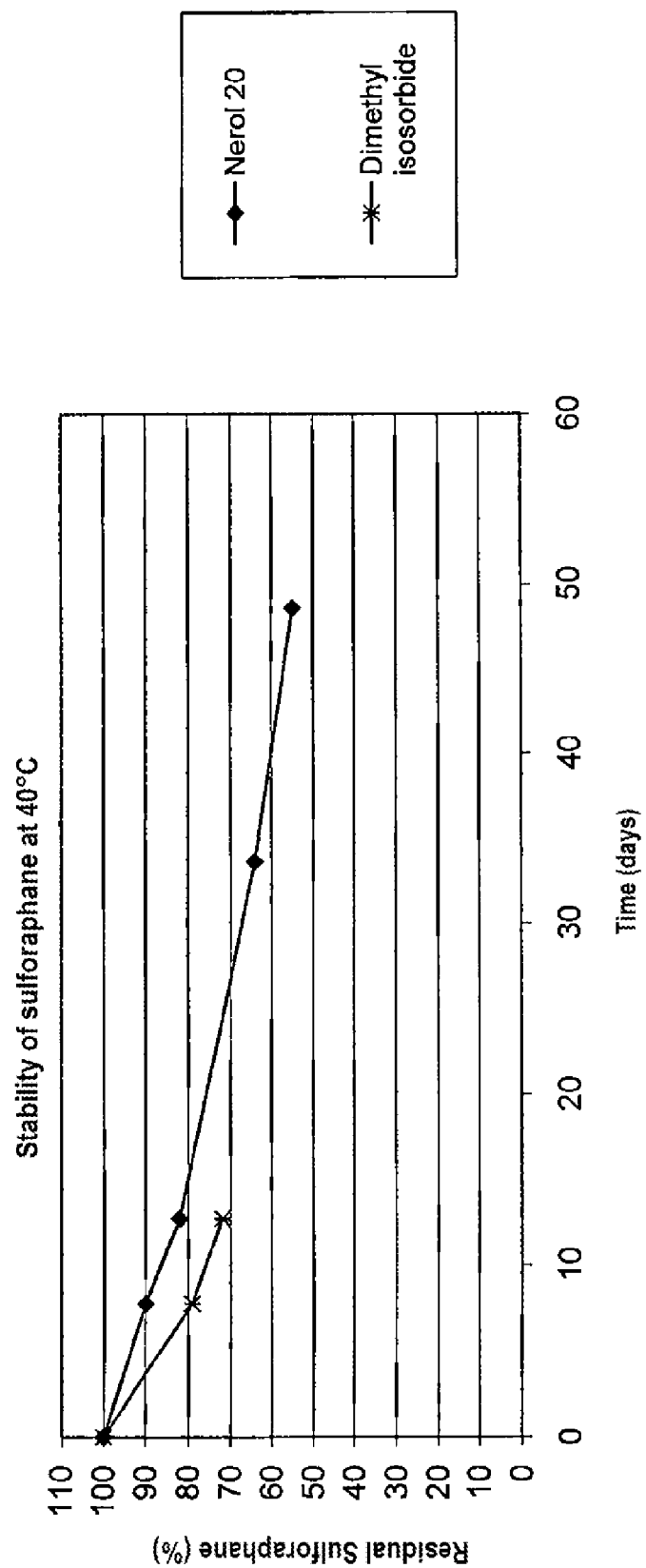
FIG. 10 illustrates the stability of sulforaphane in 2-octyl-dodecanol (Nerol 20) and in dimethyl isosorbide.

1% (m/m) sulforaphane solutions were prepared in 2-octyl-dodecanol (Nerol 20), a fatty alcohol and dimethyl isosorbide which is an ether derivative compatible with cosmetics. Kinetic tracking of the degradation was then carried out by using as an external standard naphthalene like above. As this may be seen in FIG. 10, sulforaphane is degraded over time and does not allow commercial use of this support.

EXAMPLE 1

Stabilization of Sulforaphane in Various Cosmetically and Pharmaceutically Acceptable Anhydrous Esters with Chains Free from Reactive or Free Groups or Functions In order to get rid of these problems of variability and influence of various nucleophilic agents which may be present in small amounts in the oils, but however contributing to degradation of our active substance, we tried to evaluate the degradation of sulforaphane in pure molecules.

Thus, we selected several esters customarily used in cosmetics and available without reactive groups such as ester 610, methyl salicylate or further isoamyl salicylate.

1% m/m sulforaphane solutions were prepared in each anhydrous ester mentioned above. Kinetic tracking of the degradation was then carried out at 40° C. by using naphthalene as an external standard.

Figure 6:
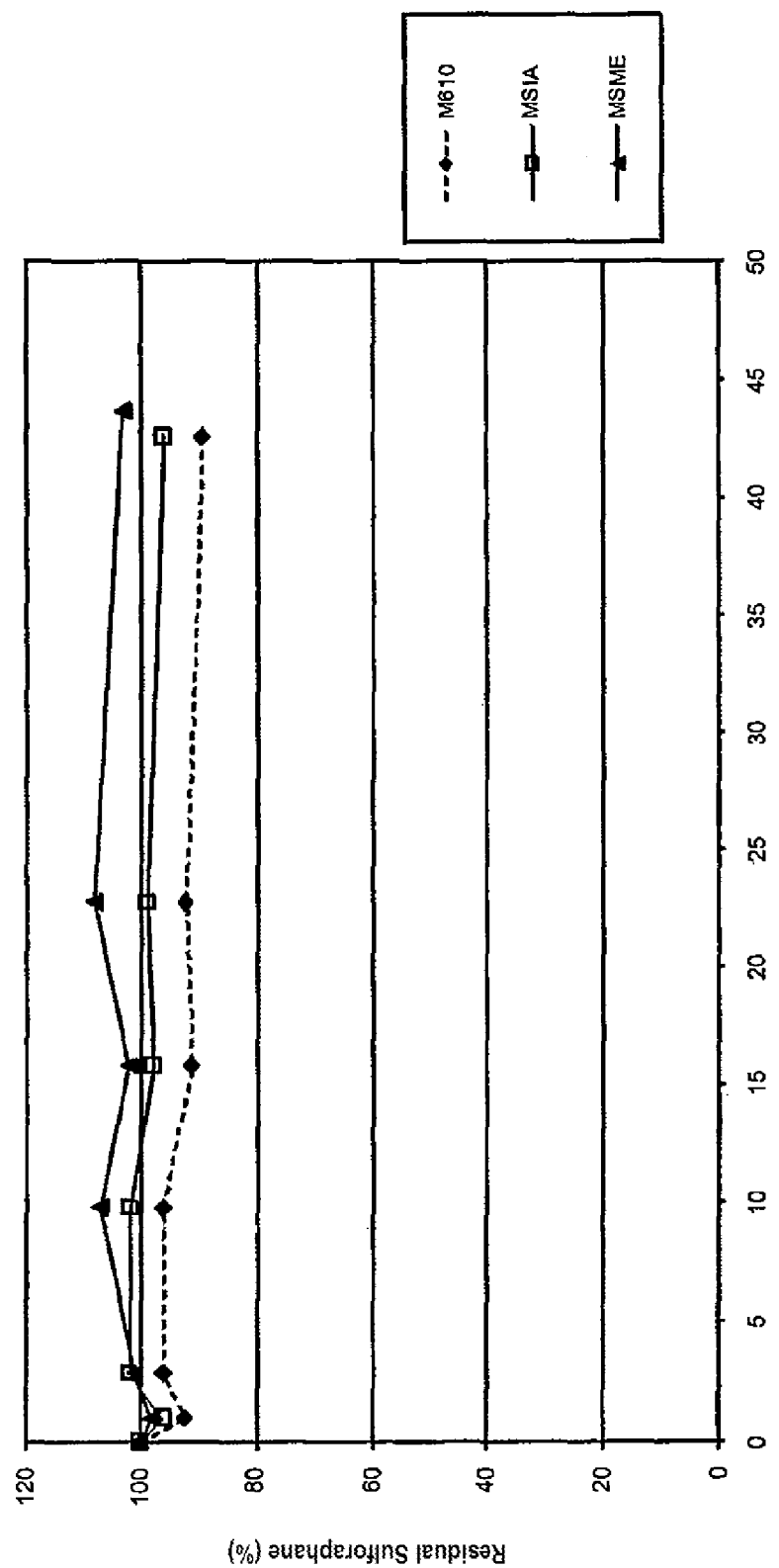
FIG. 6 illustrates the stability of sulforaphane in a cosmetically and pharmaceutically acceptable anhydrous ester with chains free from free and/or reactive groups or functions, according to the invention.

As this may be seen in FIG. 6, the observed degradation is negligible and allows the conclusion to be drawn that the matrix of choice allowing use of sulforaphane in a galenic composition mainly consists of anhydrous esters with chains free from reactive or free groups or functions compatible with the contemplated cosmetic and pharmaceutical applications. With these compounds allow solubility (>6% (m/m)) and stability may be combined.

EXAMPLE 2

Stabilization of Sulforaphane with Tocopheryl Acetate

Tocopheryl acetate has the following formula:

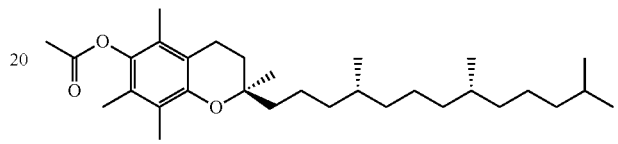

As this may be seen, tocopheryl acetate does not have any free nucleophilic function and is a matrix which may be applied in cosmetic products.

Figure 7:
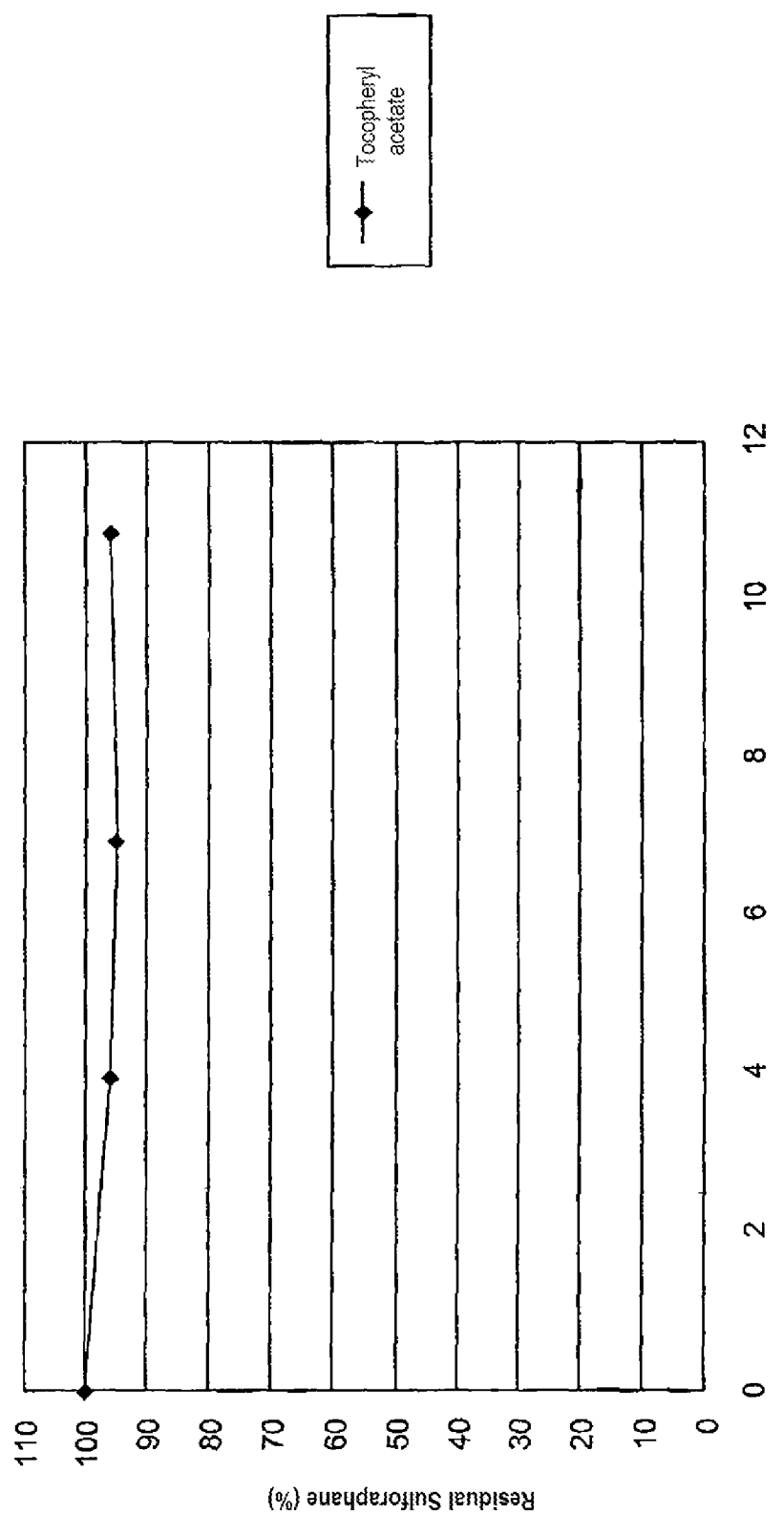
FIG. 7 illustrates the stability of sulforaphane in tocopheryl acetate.

As this may be seen, no significant degradation is observed (FIG. 7).

EXAMPLE 3

Stabilization of Sulforaphane in a Medium Containing 2 Anhydrous Esters with Chains Free from Reactive or Free Groups or Functions and at Least One Methylpolysiloxane 2 galenic formulations containing 2% of sulforaphane were prepared, a first anhydrous ester with chains free from free and/or reactive groups or functions and a second anhydrous ester with chains free from free and/or reactive groups or functions having a surfactant role, as well as a methylpolysiloxane A or B.

The test methods are the same as in Examples 1 and 2.

Figure 8:
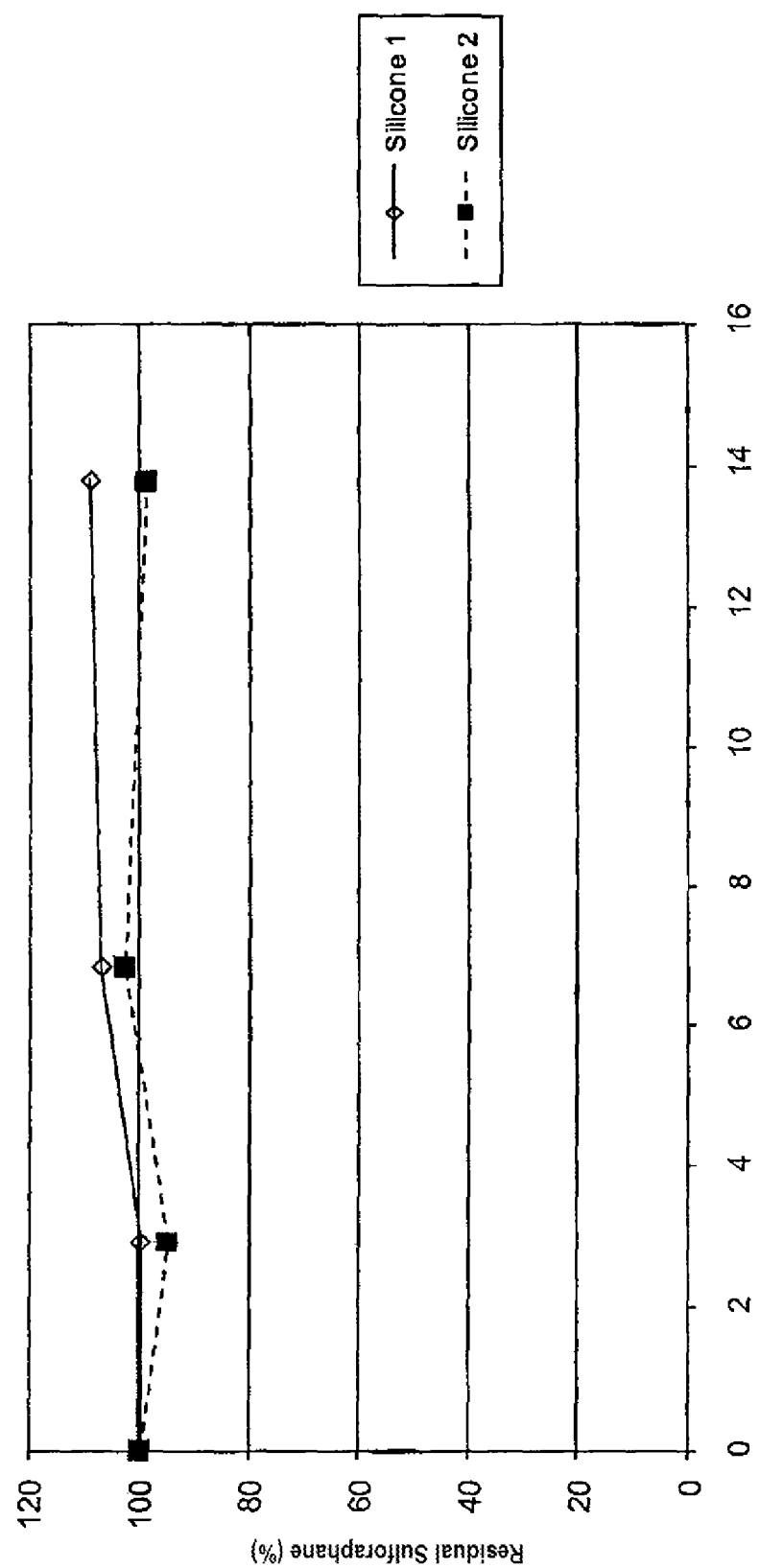
FIG. 8 illustrates the stability of sulforaphane in a galenic composition according to the invention.

As this may be seen in FIG. 8, no degradation is observed in the galenic formulation according to the invention and further the cosmetic matrix is particularly suitable for topical application.

EXAMPLE 4

Stabilization of Sulforaphane in Isostearates and in Coco Caprylate-Caprate CCC

1% (m/m) sulforaphane solutions were prepared in triethylpropane triostearate and in a product of the coco caprylate-caprate type CCC which is an ester comprised in materials of natural origin or in substitutes for synthetic esters.

Kinetic tracking of the degradation was then carried out at 40° C. by using naphthalene, as an external standard.

Figure 9:
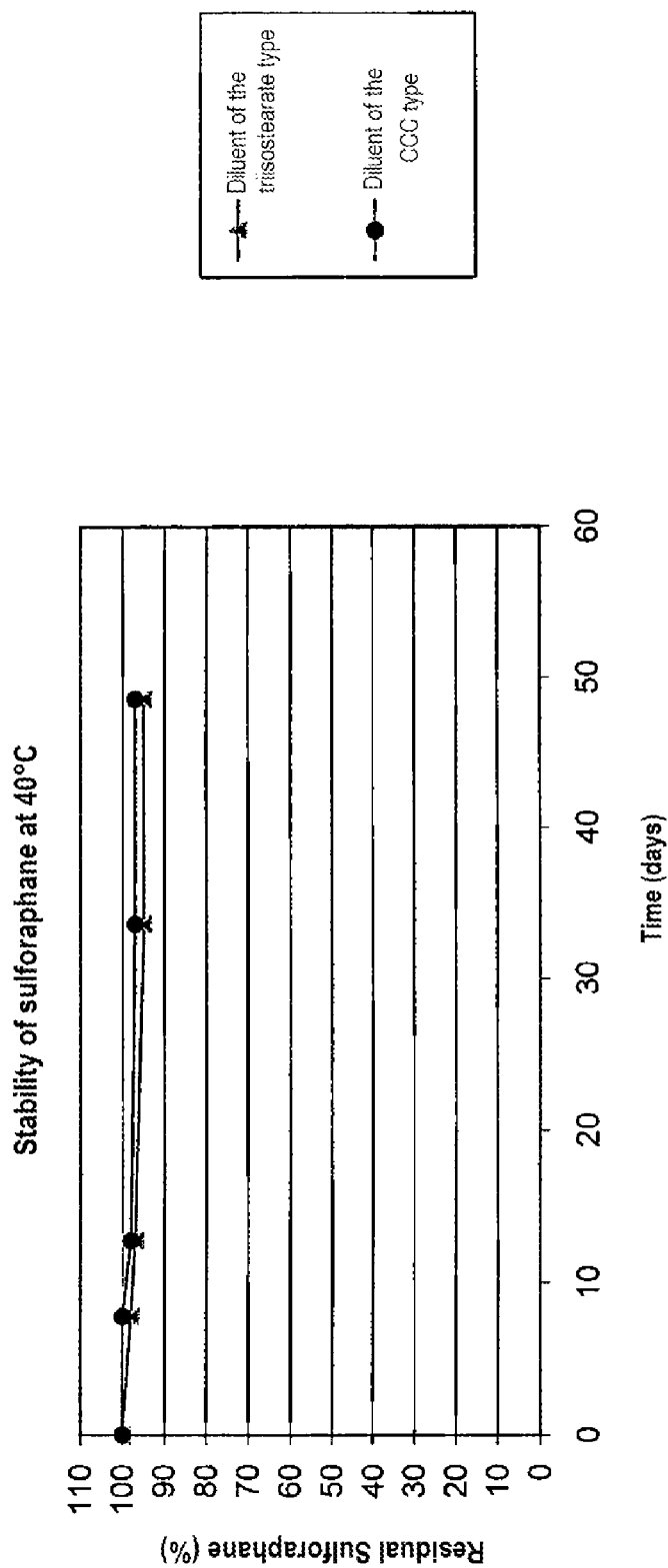
FIG. 9 illustrates the stability of sulforaphane in triethylpropane triostearate and in coca caprylate-caprate.

As this may be seen in FIG. 9, the observed degradation is negligible and allows the conclusion to be drawn that the matrix of choice which allows use of sulforaphane in a galenic composition mainly consists of pure and anhydrous esters compatible with the contemplated cosmetic and pharmaceutical applications. With these compounds, solubility (>6% (m/m)) and stability may be combined.

EXAMPLE 5

Cosmetic Formulation Based on Sulforaphane

2% (m/m) sulforaphane solutions were prepared in a mixture of isoamyl salicylate, capric/caprylic triglyceride and a derivative of the silicone type (decamethyl cyclopentasiloxane for example). It was observed that the mixture of the three compounds gave the possibility of obtaining 2% solubilization of sulforaphane, good penetration into the skin, stability of the active substance and smooth and pleasant texture during application. The stability was tracked over 6 months at 40° C. No significant degradation is observed (<3-5%/variability of the HPLC method used).

It is quite understood that the present invention is by no means limited to the embodiments described above and that many modifications may be made thereto without departing from the scope of the appended claims.

For example, addition of a perfume may be contemplated in order to cover the unpleasant but non-persisting smell of the active substance. In order not to destabilize the active molecule, it may itself be also selected from the family of esters which are numerous in having pleasant odor properties (examples: manzanate, dihydrofloralate, cyclohexylethyl acetate, . . . ).

The invention claimed is:

1. A stable galenic composition of a compound of general formula (I) wherein $R_1$ and $R_2$ both represent independently of each other an alkyl, aryl, arylalkyl group optionally substituted with one or more linear or branched, optionally cyclic groups, optionally bearing one or more heteroatoms,

 (I)

consisting of said compound of formula (I) in an amount ranging from 0.01% to 15% by weight based on the total weight of the composition
at least one cosmetically and pharmaceutically acceptable anhydrous ester, the main chain and/or the branched chains of which are free from free and/or reactive groups or functions, in an amount ranging from 0.1 to 99.9% by weight based on the total weight of the composition, and
optionally at least one cosmetically and pharmaceutically acceptable excipient for completing the 100% of the total weight of the composition, wherein said at least one cosmetically and pharmaceutically acceptable excipient is of the non-aqueous, non nucleophilic, non-hygroscopic and non hydrated type.

2. The composition according to claim 1, wherein said at least one cosmetically and pharmaceutically acceptable anhydrous ester is selected from the group consisting of acetates, benzoates, salicylates, ester 610, caprylic/capric/succinic triglycerides, stearates and isostearates, ethyl hexanoates, palmitates, isononanoates, oleates, neopentanoates, myristates and the like and mixtures thereof.

3. The composition according to claim 1, wherein $R_1$ represents a butyl group and $R_2$ represents a methyl group, said compound of general formula (I) being sulforaphane.

4. The composition according to claim 3, wherein said sulforaphane is an extracted natural sulforaphane or synthetic sulforaphane.

5. The composition according to claim 1, wherein said at least one cosmetically and pharmaceutically acceptable excipient is a methylpolysiloxane.

6. A method for forming the stable composition according to claim 1 comprising a step for mixing a compound of general formula (I) wherein $R_1$ and $R_2$ both represent independently of each other, an alkyl, aryl, arylalkyl group, optionally substituted with one or more linear or branched, optionally cyclic groups, optionally bearing one or more heteroatoms,

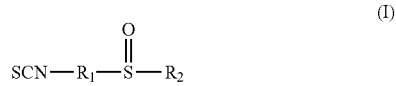 (I)

in an amount of 0.01% to 15% based on the total weight of the composition with a cosmetically and pharmaceutically acceptable anhydrous ester with chains free from free and/or reactive groups or functions, in an amount ranging from 0.1 to 99.9% by weight based on the total weight of the composition, and optionally at least one cosmetically and pharmaceutically acceptable excipient for completing the 100% of the total weight of the composition, wherein said at least one cosmetically and pharmaceutically acceptable excipient is of the non-aqueous, non-nucleophilic, non-hygroscopic and non hydrated type.

7. The method according to claim 6, wherein the cosmetically and pharmaceutically acceptable anhydrous ester, is selected from the group consisting of acetates, benzoates, salicylates, ester 610, caprylic/capric/succinic triglycerides, stearates and isostearates, ethyl hexanoates, palmitates, isononanoates, oleates, neopentanoates, myristates and the like and mixtures thereof.

8. The method according to claim 6, wherein $R_1$ represents a butyl group and $R_2$ represents a methyl group, said compound of general formula (I) being sulforaphane.

9. The method according to claim 8, wherein said sulforaphane is an extracted natural sulforaphane or synthetic sulforaphane.

10. The method according to claim 6, wherein said at least one cosmetically and pharmaceutically acceptable excipient is a methylpolysiloxane.

* * * * *